(12) United States Patent
Hsiao et al.

(10) Patent No.: US 11,992,290 B2
(45) Date of Patent: May 28, 2024

(54) INTRAORAL SCANNER AND METHOD OF CONTROLLING SAME

(71) Applicant: QISDA CORPORATION, Taoyuan (TW)

(72) Inventors: Yuan-Yu Hsiao, New Taipei (TW); Ching-Ting Liu, Taipei (TW)

(73) Assignee: Qisda Corporation, Taoyuan (TW)

( * ) Notice: Subject to any disclaimer, the term of this patent is extended or adjusted under 35 U.S.C. 154(b) by 756 days.

(21) Appl. No.: 16/985,213

(22) Filed: Aug. 4, 2020

(65) Prior Publication Data

US 2021/0052163 A1 Feb. 25, 2021

(30) Foreign Application Priority Data

Aug. 22, 2019 (CN) .......................... 201910780362.X

(51) Int. Cl.
*A61B 5/00* (2006.01)
*A61B 1/24* (2006.01)
*G06T 7/00* (2017.01)

(52) U.S. Cl.
CPC .............. *A61B 5/0088* (2013.01); *A61B 1/24* (2013.01); *G06T 7/0012* (2013.01); *G06T 2207/30036* (2013.01)

(58) Field of Classification Search
CPC ....... A61B 5/0088; A61B 7/24; G06T 7/0012; G06T 2207/30036
See application file for complete search history.

(56) References Cited

U.S. PATENT DOCUMENTS

| 10,543,065 | B2* | 1/2020 | Lin | A61B 1/00036 |
| 2008/0063998 | A1* | 3/2008 | Liang | G01B 11/2441 |
| | | | | 433/29 |
| 2009/0298017 | A1* | 12/2009 | Boerjes | A61B 5/4547 |
| | | | | 433/214 |
| 2012/0013722 | A1* | 1/2012 | Wong | G01J 3/0224 |
| | | | | 348/66 |
| 2022/0133446 | A1* | 5/2022 | Tao | A61B 5/0066 |
| | | | | 433/29 |
| 2022/0233284 | A1* | 7/2022 | Fridman | A61B 1/00034 |
| 2022/0240786 | A1* | 8/2022 | Subhash | A61C 19/04 |
| 2023/0068727 | A1* | 3/2023 | Saphier | A61C 9/006 |

FOREIGN PATENT DOCUMENTS

| CN | 104990518 A | 10/2015 |
| CN | 105496444 A | 4/2016 |
| CN | 206930271 U | 1/2018 |

* cited by examiner

*Primary Examiner* — Nicholas D Lucchesi

(57) ABSTRACT

A method of controlling an intraoral scanner includes upon completion of lighting a first projection device, triggering a second projection device to initiate lighting, upon initiation of lighting the first projection device, transmitting a first camera trigger signal, a first delay circuit delaying the first camera trigger signal until completion of lighting the second projection device, and upon receiving the first camera trigger signal, a first camera and a second camera starting exposing images.

4 Claims, 8 Drawing Sheets

INTRAORAL SCANNER AND METHOD OF CONTROLLING SAME

CROSS REFERENCE TO RELATED APPLICATION

This non-provisional application claims priority of China patent application No. 201910780362.X, filed on 22 Aug. 2019, included herein by reference in its entirety.

BACKGROUND OF THE INVENTION

1. Field of the Invention

The invention relates to optical scanning, and in particular, to an intraoral scanner and a method of controlling the same.

2. Description of the Prior Art

An intraoral scanner employs laser light to scan the teeth, and then employs software to build a teeth model for use of simulation or other clinical purposes. At present, the intraoral scanner only uses one projector and one camera to scan teeth, resulting in a narrow scanning area and a slow scanning speed.

Therefore, an intraoral scanner and a method of controlling the same are provide to identify the three-dimensional location information of an object under test, while increasing a scanning area and reducing a scanning time.

SUMMARY OF THE INVENTION

According to one embodiment of the invention, a method of controlling an intraoral scanner includes upon completion of lighting a first projection device, triggering a second projection device to initiate lighting, upon initiation of lighting the first projection device, transmitting a first camera trigger signal, a first delay circuit delaying the first camera trigger signal until completion of lighting the second projection device, and upon receiving the first camera trigger signal, a first camera and a second camera starting exposing images.

According to one embodiment of the invention, an intraoral scanner includes a first projection device used to project an image, a second projection device coupled to the first projection device and used to project an image, a first delay circuit coupled to the first projection device and used to delay a first camera trigger signal transmitted from the first projection device, a first camera coupled to the first delay circuit and used to capture an image, and a second camera coupled to the first delay circuit and used to capture an image. Upon completion of lighting the first projection device, the second projection device is triggered to initiate lighting. Upon initiation of lighting the first projection device, the first projection device is used to transmit a first camera trigger signal. The first delay circuit is used to delay the first camera trigger signal until completion of lighting the second projection device. Upon receiving the first camera trigger signal, the first camera and the second camera are used to start exposing images.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
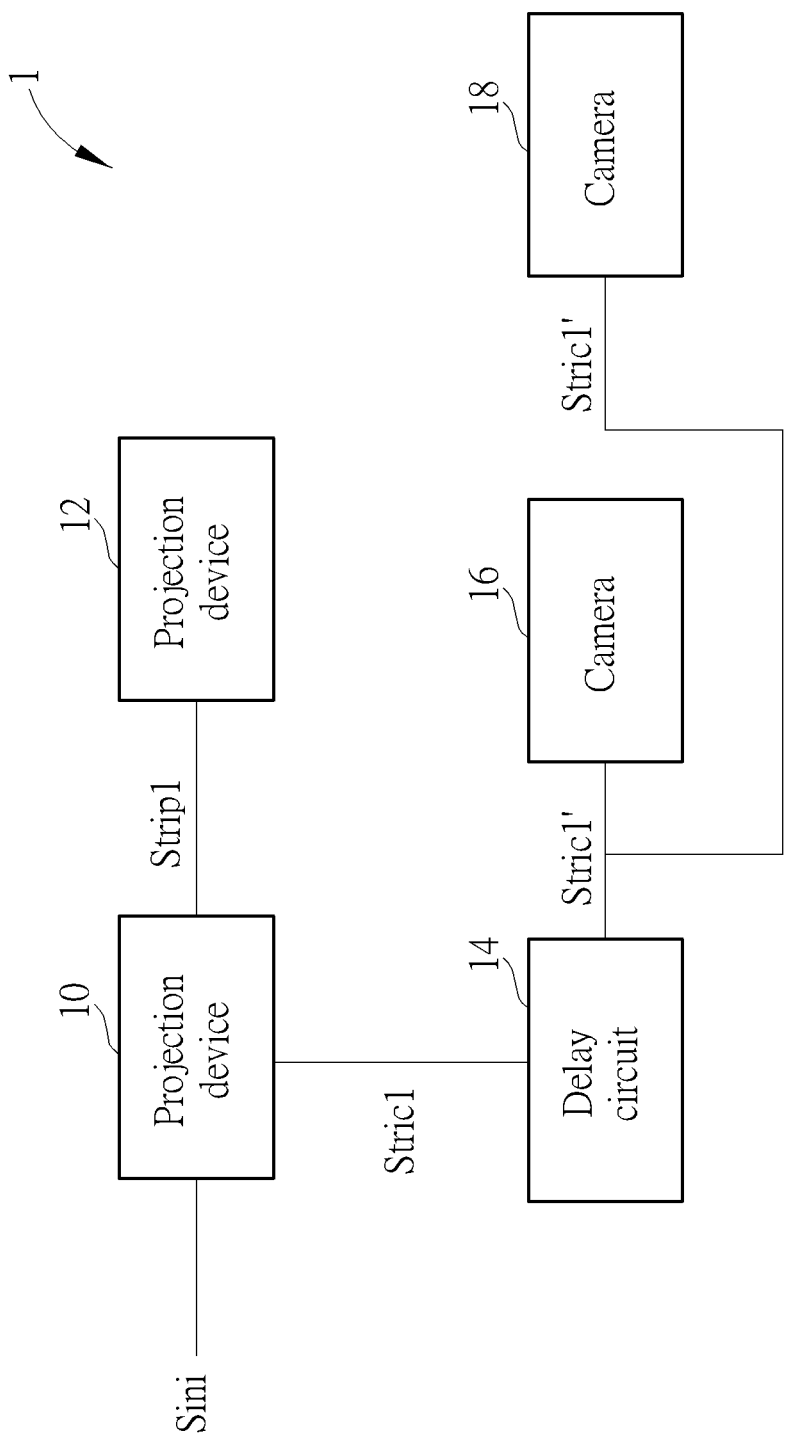
FIG. 1 is a block diagram of an intraoral scanner according to an embodiment of the invention.

FIG. 1 is a block diagram of an intraoral scanner 1 according to an embodiment of the invention. The intraoral scanner 1 may employ 2 projection devices and 2 cameras to identify three-dimensional location information of an object under test, while increasing a scanning area and reducing a scanning time.

The intraoral scanner 1 may include projection devices 10, 12, cameras 16, 18 and a delay circuit 14. The projection device 10 may be coupled to the projection device 12 and the delay circuit 14. The delay circuit 14 may be coupled to the cameras 16, 18, respectively. When in operation, the projection devices 10, 12 may respectively project a first portion and a second portion of a predetermined pattern that are adjacent to each other onto the object under test, e.g., a plurality of teeth. The cameras 16, 18 may capture images of the first portion and second portion of the predetermined pattern projected on the object under test. The projection device 10 may trigger the projection device 12 to project an image, and synchronize the cameras 16, 18 to capture images, ensuring that the projection devices 10, 12 project the same predetermined pattern and the cameras 16, 18 accurately capture the projected predetermined image. The predetermined pattern may be a structured light patter such as a grid, a stripe, a circle, a cross pattern, a gray code pattern, a color code patter, other coding patterns or random patterns. When the predetermined pattern is projected onto the surface of the object under test having different shapes, patterns and/or depth, a deformation may occur, the image captured by the cameras 16, 18 may show the first portion and the second portion of the predetermined pattern, respectively. The intraoral scanner 1 may compare the images captured by the cameras 16, 18 and the original predetermined image to obtain the three-dimensional location information of the surface of the object under test.

Upon receiving an initialization signal Sini, the projection device 10 may initiate lighting and transmit a camera trigger signal Stric1 to the delay circuit 14. Upon completion of lighting, the projection device 10 may transmit a projection device trigger signal Strip1 to trigger the projection device 12 to initiate lighting. The delay circuit 14 may delay the camera trigger signal Stric1 until the projection device 12 completing lighting, and upon the cameras 16, 18 receiving the delayed camera trigger signal Stric1', the cameras 16, 18 may start exposing images. During projection, it may take a first duration from starting lighting to completing lighting of the projection device 10, and it may take a second duration from initiating lighting to completing lighting of the projection device 12. When the projection device 10 and the projection device 12 are substantially identical, the length of the first duration is substantially equal to the length of the second duration. The delay circuit 14 may delay the camera trigger signal Stric1 for a time exceeding a sum of the first duration and the second duration. During image capture, it may take corresponding exposure durations for the cameras 16, 18 to capture images of the first portion and second portion of the predetermined pattern, respectively. When the camera 16 and the camera 18 are substantially identical, the exposure durations of the cameras 16, 18 may be substantially equal. When the camera 16 and the camera 18 are different, the exposure durations of the cameras 16, 18 may be set as the larger one of the required exposure durations of the cameras 16, 18.

Figure 2:
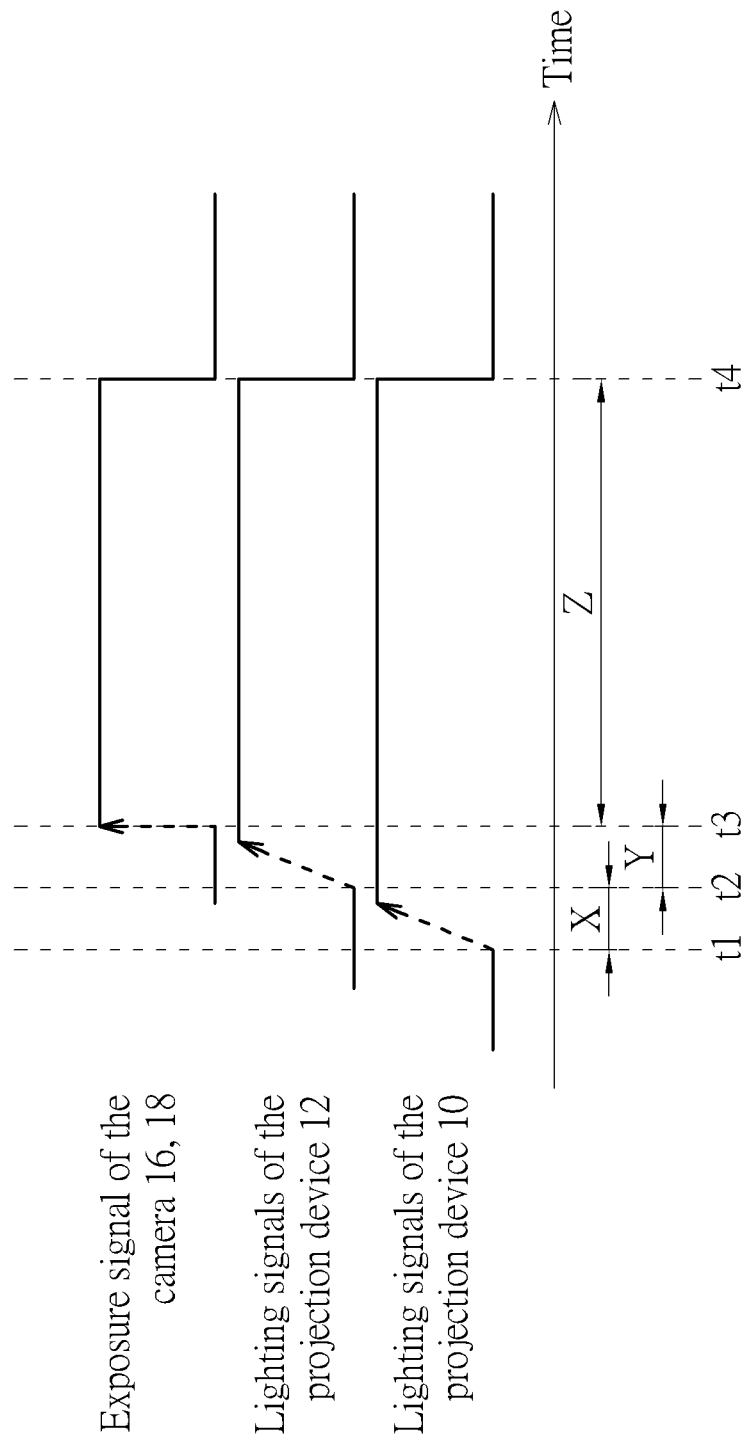
FIG. 2 is a timing diagram of selected signals of the intraoral scanner in FIG. 1.

FIG. 2 is a timing diagram of selected signals of the intraoral scanner 1, the selected signals including lighting signals of the projection devices 10, 12 and exposure signals of the cameras 16, 18. At Time t1, the projection device 10 receives the initialization signal Sini, and the lighting signal of the projection device 10 starts rising. After a duration X, at Time t2, the projection device 10 completes lighting and projecting a corresponding portion of the predetermined pattern, and transmits the projection device trigger signal Strip1 to trigger the projection device 12 to initiate lighting, and consequently, the lighting signal of the projection device 12 starts rising. The duration X is greater than or equal to the first duration of the projection device 10. After a duration Y, at Time t3, the projection device 12 also completes lighting and projecting a corresponding portion of the predetermined pattern, and the cameras 16, 18 starts exposing images in response to the exposure signals of the cameras 16, 18. The duration Y is greater than or equal to the second duration of the projection device 12. After a duration Z, at Time t4, the cameras 16, 18 have completed exposure and capturing the predetermined image, and the lighting signal of the projection device 10, the lighting signal of the projection device 12, and the exposure signals of the cameras 16, 18 are reset to turn off the projection devices 10, 12 and the cameras 16, 18. The duration Z is greater than or equal to the exposure duration of the cameras 16, 18. The intraoral scanner 1 may take a duration equal to a sum of the durations X, Y and Z to complete projection and capture of the predetermined image. In other words, projection frame rates of the projection devices 10, 12 are less than or equal to an inverse of a sum of the first duration, the second duration and exposure durations of the cameras 16, 18.

Figure 3:
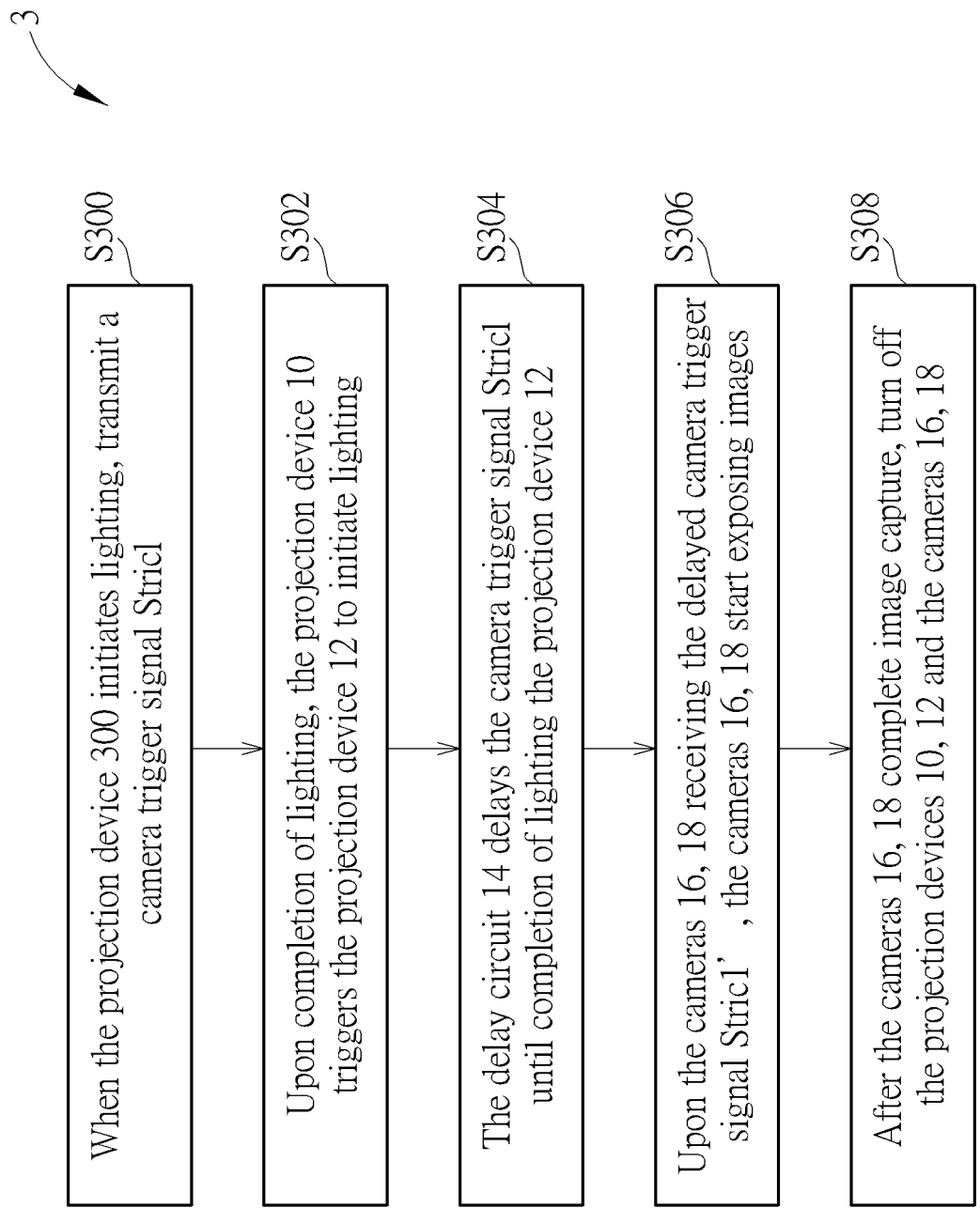
FIG. 3 is a flowchart of a method of controlling the intraoral scanner in FIG. 1.

FIG. 3 is a flowchart of a method 3 of controlling the intraoral scanner 1. The method 3 includes Steps S300 to S308, synchronizing projection of the projection devices 10, 12 and image capture of the cameras 16, 18. Step S302 is used to trigger the projection device 12 to initiate lighting, Steps S300, S304, S306 are used to synchronize the image capture of the cameras 16, 18, and Step S308 is used to turn off the projection devices 10, 12 and the cameras 16, 18. Any reasonable step change or adjustment is within the scope of the disclosure. Steps S300 to S308 are detailed as follows:

Step S300: When the projection device 300 initiates lighting, transmit a camera trigger signal Stric1;

Step S302: Upon completion of lighting, the projection device 10 triggers the projection device 12 to initiate lighting;

Step S304: The delay circuit 14 delays the camera trigger signal Stric1 until completion of lighting the projection device 12;

Step S306: Upon the cameras 16, 18 receiving the delayed camera trigger signal Stric1', the cameras 16, 18 start exposing images;

Step S308: After the cameras 16, 18 complete image capture, turn off the projection devices 10, 12 and the cameras 16, 18.

The explanation for Steps S300 to S308 has been provided in the preceding paragraph and will be omitted here for brevity. By employing Steps S300 to S308, the intraoral scanner 10 triggers the projection devices 10 to project an image and the cameras 16, 18 to capture images, thereby accurately identifying the three-dimensional location information of an object under test, while increasing a scanning area and reducing a scanning time.

While two projection devices and cameras are used in the embodiment, the intraoral scanner 1 may also be implemented by more than two projection devices and cameras. For example, when the intraoral scanner 1 employs three projection devices and cameras, the projection device 10 may transmit the projection device trigger signal Strip1 upon completion of lighting, so as to synchronize projection of the other 2 projection devices, and may transmit the camera trigger signal Stric1 upon initiation of lighting to synchronize image capture of the 3 cameras. The intraoral scanner 1 and the method 3 may employ the projection device 10 to trigger projection of the projection device 12 and image capture of the cameras 16, 18 without using a processing unit, accurately identifying three-dimensional location information of an object under test, while increasing a scanning area and reducing a scanning time.

Figure 4:
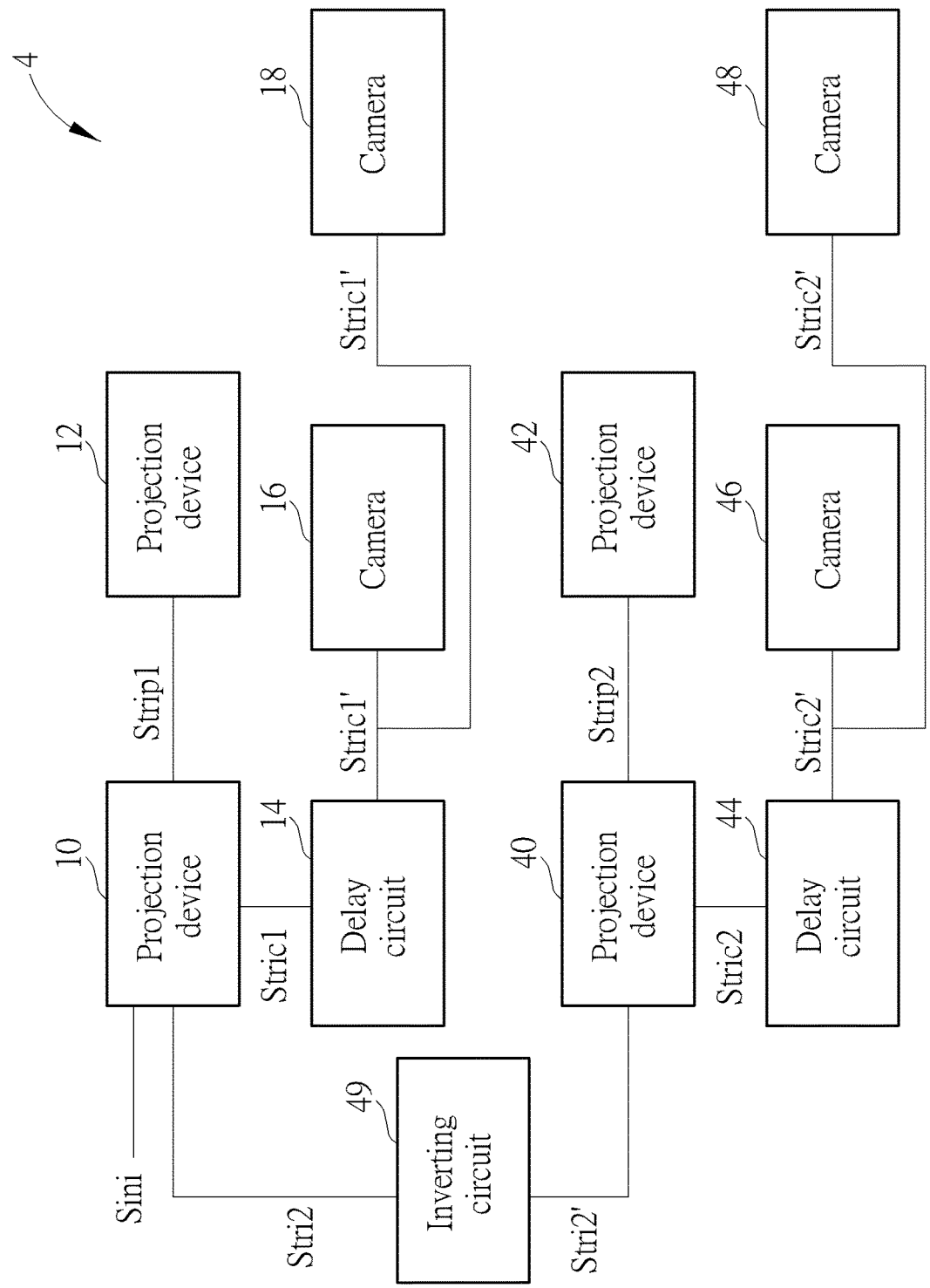
FIG. 4 is a block diagram of an intraoral scanner according to another embodiment of the invention.

FIG. 4 is a block diagram of an intraoral scanner 4 according to another embodiment of the invention. The intraoral scanner 4 includes projection devices 10, 12, 40, 42, cameras 16, 18, 46, 48, delay circuits 14, 44 and an inverting circuit 49. The projection devices 10, 12, 40, 42, the cameras 16, 18, 46, 48, and the delay circuits 14, 44 may be divided into two groups, alternately performing operations associated with two sets of interleaved patterns of predetermined images. The projection devices 10, 12, the cameras 16, 18 and the delay circuit 14 may belong to a first group, projecting and capturing images of a first set of interleaved patterns of the predetermined patterns. and the projection devices 40, 42, the cameras 46, 48 and the delay circuit 44 may belong to a second group, projecting and capturing images of a second set of interleaved patterns of the predetermined patterns. The first set of interleaved patterns may include a first predetermined pattern and a second predetermined pattern, and the second set of interleaved patterns may include a third predetermined pattern and a fourth predetermined pattern. The first predetermined pattern and the third predetermined pattern are interleaved to each other, and the second predetermined pattern and the fourth predetermined pattern are interleaved to each other. The first group and the second group may be coupled to each other via the inverting circuit 49. The operations and the configurations of the projection devices 10, 12, the cameras 16, 18 and the delay circuit 14 of the intraoral scanner 4 may be similar to those of the intraoral scanner 1, and the explanation therefor will be omitted here for brevity.

The projection device 10 may be coupled to the inverting circuit 49. The inverting circuit 49 may be coupled to the projection device 40. The projection device 40 may be coupled to the projection device 42 and the delay circuit 44. The delay circuit 44 may be coupled to the cameras 46, 48, respectively. The projection device 10 in the first group may trigger the projection device 40 in the second group via the inverting circuit 49 to project an image. The projection device 40 may trigger the projection device 42 to project and synchronize the cameras 46, 48 to capture images, synchronizing projection and capture of the third predetermined image and the fourth predetermined image. The projection devices 40, 42 may project the third predetermined image and the fourth predetermined image onto the object under test, respectively. The cameras 46, 48 may capture images of the third predetermined image and the fourth predetermined image projected on the object under test.

Upon the projection device 10 being turned off, the projection device 10 may transmit a trigger signal Stri2 to the inverting circuit 49. For example, upon turning off, the projection device 10 may set a rising edge or a falling edge in the trigger signal Stri2. The inverting circuit 49 may generate an inverted trigger signal Stri2', e.g., a rising edge or a falling edge in the inverted trigger signal Stri2' to trigger the projection device 40 to initiate lighting. Upon completion of lighting, the projection device 40 triggers the projection device 42 to initiate lighting; Upon receiving the inverted trigger signal Stri2', the projection device 40 may initiate lighting and transmit a camera trigger signal Stric2 to the delay circuit 44, and the delay circuit 44 may delay the camera trigger signal Stric2 until the completion of lighting the projection device 42. Upon the cameras 46, 48 receiving the delayed camera trigger signal Stric2', the cameras 46, 48 may start exposing images; During projection, it may take a third duration from initiating lighting to completing lighting of the projection device 40, and it may take a fourth duration from initiating lighting to completing lighting of the projection device 42. When the projection device 40 and the projection device 42 are substantially identical, the length of the third duration is substantially equal to the length of the fourth duration. The delay circuit 44 may delay the camera trigger signal Stric2 for a time exceeding a sum of the third duration and the fourth duration. During image capture, it may take corresponding exposure durations for the cameras 46, 48 to capture images of the third predetermined image and the fourth predetermined image, respectively. When the camera 46 and the camera 48 are substantially identical, the exposure durations of the cameras 46, 48 may be substantially equal. When the camera 46 and the camera 48 are different, the exposure durations of the cameras 46, 48 may be set as the larger one of the required exposure durations of the cameras 46, 48.

Figure 5:
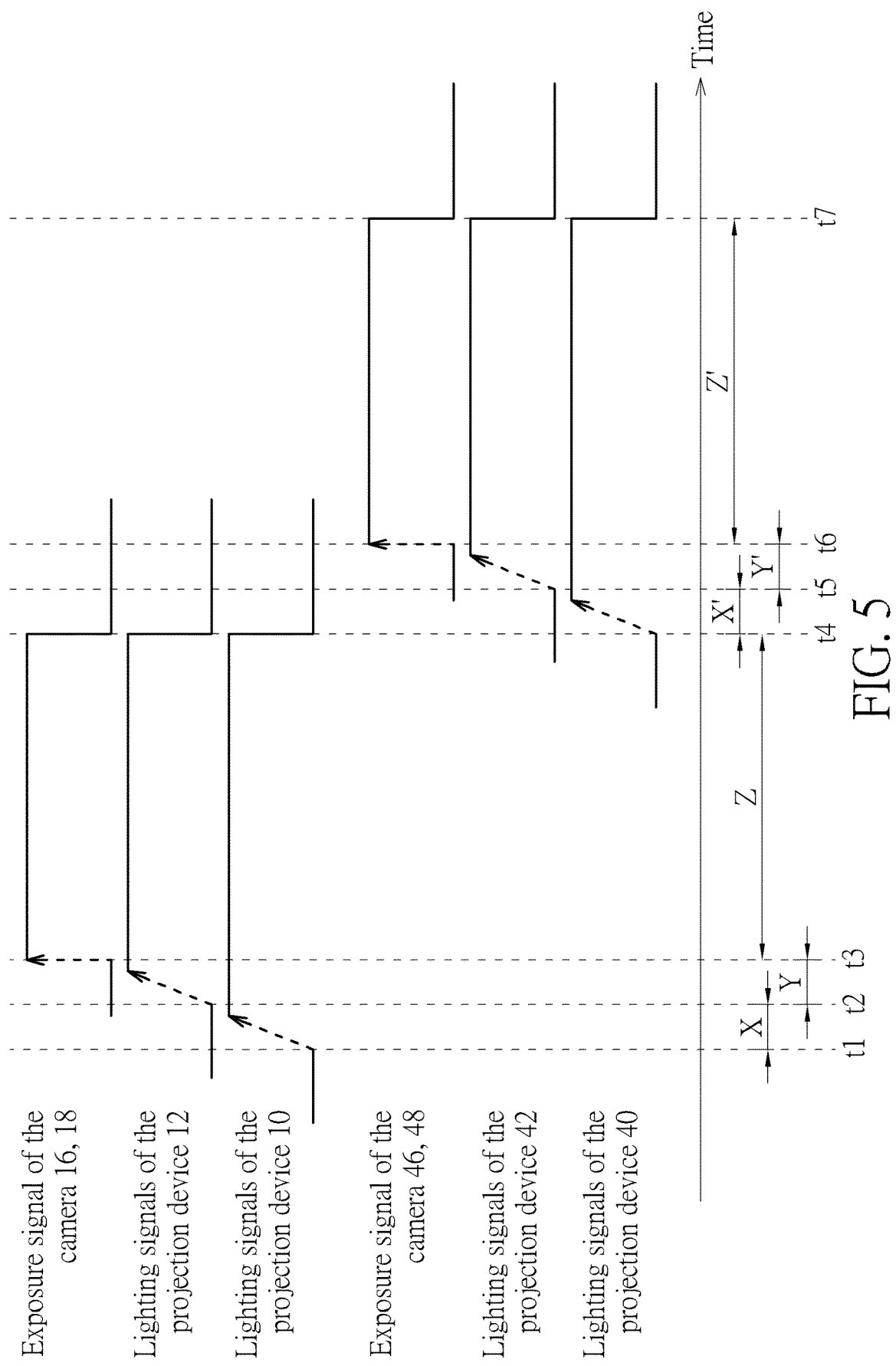
FIG. 5 is a timing diagram of selected signals of the intraoral scanner in FIG. 4.

FIG. 5 is a timing diagram of selected signals of the intraoral scanner 4, the selected signals including lighting signals of the projection devices 10, 12, 40, 42 and exposure signals of the cameras 16, 18, 46, 48. The operations of the lighting signals of the projection devices 10, 12 and the exposure signals of the cameras 16, 18 in FIG. 5 are similar to those in FIG. 2, and the explanation therefor will be omitted for brevity. At Time t4, the projection device 10 is turned off and the inverting circuit 49 triggers the projection device 40 via the inverted trigger signal Stri2' to initiate lighting. Upon the projection device 40 receiving the inverted trigger signal Stri2', the lighting signal of the projection device 40 starts rising. After a duration X', at Time t5, the projection device 40 completes lighting and projecting the third predetermined pattern, and transmits the projection device trigger signal Strip2 to trigger the projection device 42 to initiate lighting, and consequently, the lighting signal of the projection device 42 starts rising. The duration X' is greater than or equal to the third duration of the projection device 40. After a duration Y', at Time t6, the projection device 42 also completes lighting and projecting the fourth predetermined pattern, and the cameras 46, 48 start exposing images in response to the exposure signals of the cameras 46, 48. The duration Y' is greater than or equal to the fourth duration of the projection device 42. After a duration Z', at Time t7, upon the cameras 46, 48 completing exposure and capturing the third predetermined image and the fourth predetermined image, the lighting signal of the projection device 40, the lighting signal of the projection device 42, and the exposure signals of the cameras 46, 48 are reset to turn off the projection devices 40, 42 and the cameras 46, 48. The duration Z' is greater than or equal to the exposure duration of the cameras 46, 48. The intraoral scanner 4 may take a duration equal to a sum of the durations X, Y, Z, X', Y' and Z' to complete projecting and capturing the predetermined image. In other words, projection frame rates of the projection devices 10, 12, 40, 42 are less than or equal to an inverse of a sum of the first duration, the second duration, the third duration, the fourth duration and exposure durations of the cameras 16, 18, 46, 48.

Figure 6:
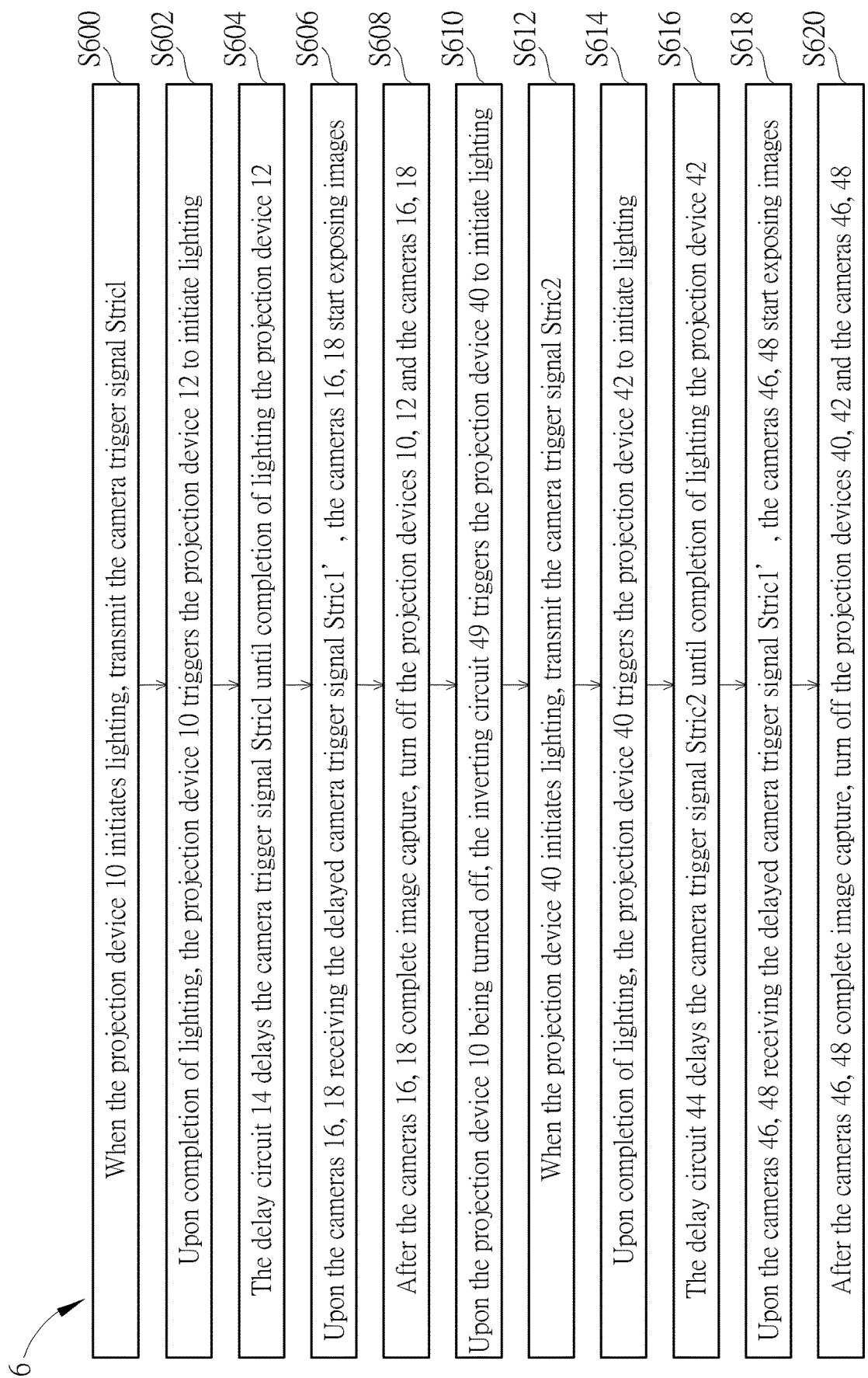
FIG. 6 is a flowchart of a method of controlling the intraoral scanner in FIG. 4.

FIG. 6 is a flowchart of a method 6 of controlling the intraoral scanner 4. The method 6 includes Steps S600 to S620. Step S600 to S606 are used to synchronize projection and image capture of the projection devices 10, 12 and the cameras 16, 18 in the first group. Step S608 is used to turn off the projection devices 10, 12 and the cameras 16, 18. Steps S610 to S618 are used to synchronize projection and image capture of the projection devices 40, 42 and the cameras 46, 48 in the first group. Step S620 is used to turn off the projection devices 40, 42 and the cameras 46, 48. Any reasonable step change or adjustment is within the scope of the disclosure. Steps S600 to S620 are detailed as follows:

Step S600: When the projection device 10 initiates lighting, transmit the camera trigger signal Stric1;

Step S602: Upon completion of lighting, the projection device 10 triggers the projection device 12 to initiate lighting;

Step S604: The delay circuit 14 delays the camera trigger signal Stric1 until completion of lighting the projection device 12;

Step S606: Upon the cameras 16, 18 receiving the delayed camera trigger signal Stric1', the cameras 16, 18 start exposing images;

Step S608: After the cameras 16, 18 complete image capture, turn off the projection devices 10, 12 and the cameras 16, 18;

Step S610: Upon the projection device 10 being turned off, the inverting circuit 49 triggers the projection device 40 to initiate lighting;

Step S612: When the projection device 40 initiates lighting, transmit the camera trigger signal Stric2;

Step S614: Upon completion of lighting, the projection device 40 triggers the projection device 42 to initiate lighting;

Step S616: The delay circuit 44 delays the camera trigger signal Stric2 until completion of lighting the projection device 42;

Step S618: Upon the cameras 46, 48 receiving the delayed camera trigger signal Stric1', the cameras 46, 48 start exposing images;

Step S620: After the cameras 46, 48 complete image capture, turn off the projection devices 40, 42 and the cameras 46, 48.

The explanation for Steps S600 to S620 has been provided in the preceding paragraph and will be omitted here for brevity. By employing Steps S600 to S620, the projection device 10 may control projection and image capture of the projection devices 10, 12 and the cameras 16, 18 in the first group, and control projection and image capture of the projection devices 40, 42 and the cameras 46, 48 in the second group, thereby accurately identifying the three-dimensional location information of an object under test without employing a processing unit, while increasing a scanning area and reducing a scanning time.

While two groups of projection devices and cameras are used to implement the intraoral scanner 4 in the embodiment, the intraoral scanner 4 may be implemented by more than two groups of projection devices and cameras. In some embodiments, when the intraoral scanner 4 employs three groups of projection devices and cameras, the projection device 10 may turn off a first group of projection devices and cameras while triggering projection and image capture of a second group of projection devices and cameras upon completion of projection and image capture of the first group, and the projection device 40 may turn off the second group of projection devices and cameras while triggering projection and image capture of a third group of projection devices and cameras upon completion of projection and image capture of the second group. The first, second and third groups of projection devices and cameras may project and capture first, second and third sets of predetermined patterns, and the first, second and third sets of predetermined patterns may be interleaved with each other.

Figure 7:
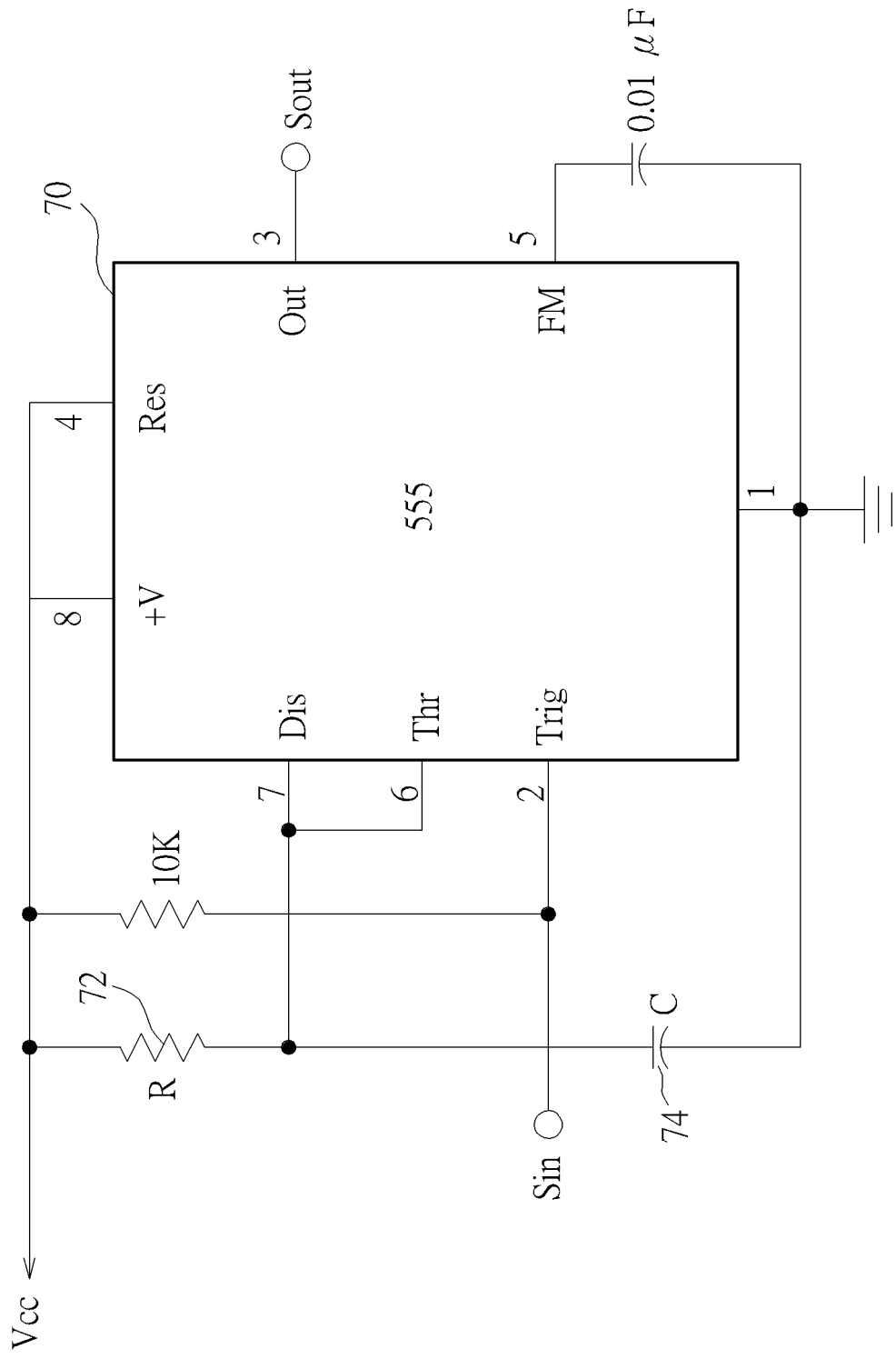
FIG. 7 is a circuit schematic of the delay circuit of the intraoral scanner in FIG. 1 or 4.

FIG. 7 is a circuit schematic of the delay circuit 14 or 44 of the intraoral scanner 1 or 4. The delay circuit 14 or 44 may be implemented by a timer chip 70. The timer chip 70 may receive a trigger signal Sin, and delay the trigger signal Sin for a delay time to generate a delayed trigger signal Sout. The length of the delay time is determined by a product of the resistance R of a resistor 72 and the capacitance C of a capacitor 74. In some embodiments, the delay time has a time length T of 1.1*R*C, that is, after the time length T upon receiving the trigger signal Sin, the timer chip 70 may generate the delayed trigger signal Sout.

Figure 8:
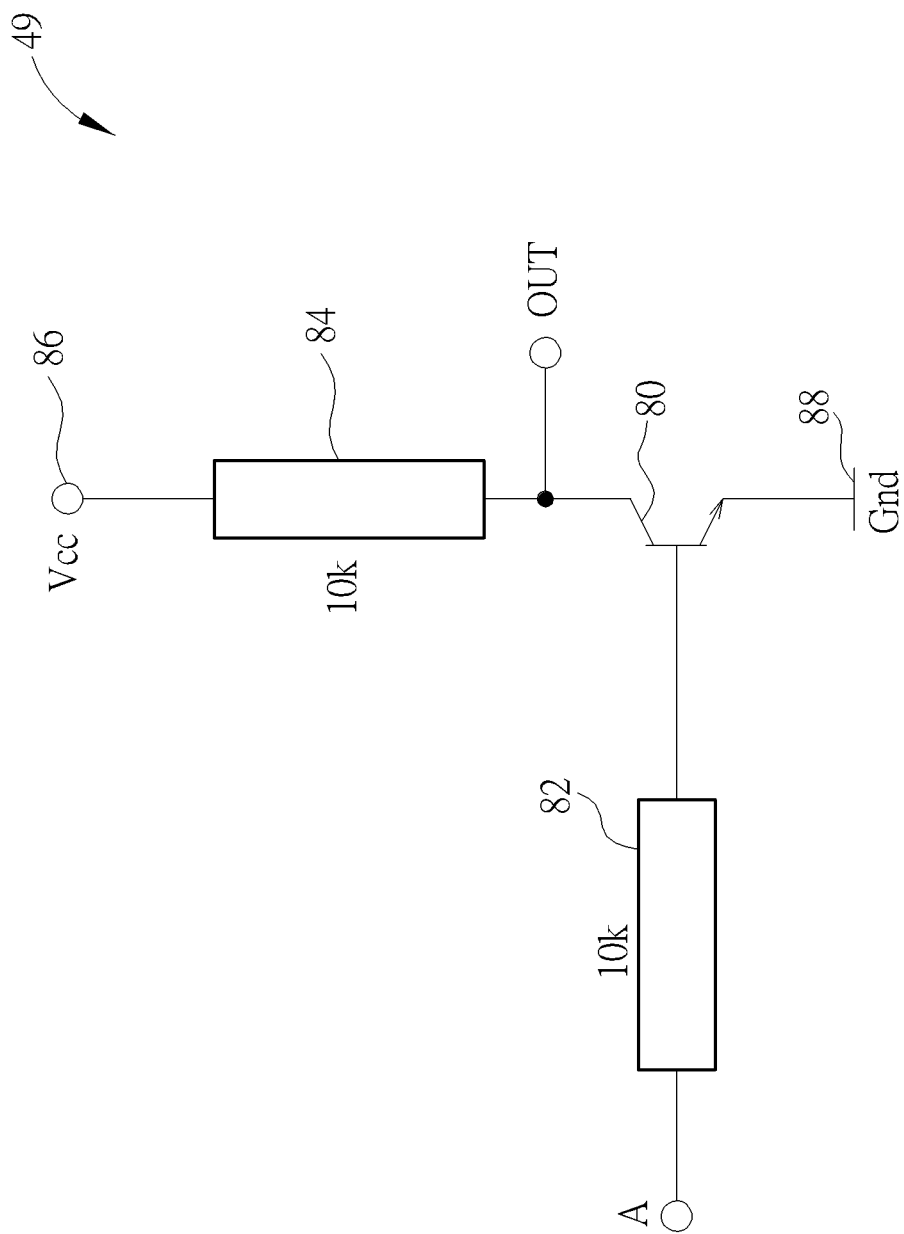
FIG. 8 is a circuit schematic of the inverting circuit of the intraoral scanner in FIG. 4.

FIG. 8 is a circuit schematic of the inverting circuit 49 of the intraoral scanner 4. The inverting circuit 49 includes a transistor 80, resistors 82, 84, a supply voltage terminal 86 and a common voltage terminal 88. The transistor 80 may be a bipolar junction transistor configured into a common emitter, including a control terminal, a first terminal and a second terminal. The control terminal of the transistor 80 may receive an input signal A via a resistor 82. The first terminal of the transistor 80 may be coupled to the supply voltage terminal 86 via the resistor 84, and may output an inverse of the input signal A as the output signal OUT. The second terminal of the transistor 80 may be coupled to the common voltage terminal 88. The supply voltage terminal 86 may provide a supply voltage. The common voltage terminal 88 may provide a ground voltage Gnd.

The intraoral scanners 1, 4 and the methods 3, 6 may employ the projection device 1 to trigger projection of the projection device 10 and synchronize image capture of cameras without using a processing unit, accurately identifying three-dimensional location information of an object under test, while increasing a scanning area and reducing a scanning time.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A method of controlling an intraoral scanner, the method comprising:
   upon completion of lighting a first projection device, triggering a second projection device to initiate lighting;
   upon initiation of lighting the first projection device, transmitting a first camera trigger signal;
   a first delay circuit delaying the first camera trigger signal until completion of lighting the second projection device;
   upon receiving the first camera trigger signal, a first camera and a second camera starting capturing images;
   upon completion of the first camera and the second camera capturing the images, turning off the first projection device, the second projection device, the first camera and the second camera;
   when the first projection device is turned off, triggering a third projection device to initiate lighting;
   upon completion of lighting the third projection device, triggering a fourth projection device to initiate lighting;
   when the third projection device initiates lighting, transmitting a second camera trigger signal;
   a second delay circuit delaying the second camera trigger signal until completion of lighting the fourth projection device; and
   when a third camera and a fourth camera receive the second camera trigger signal, the third camera and the fourth camera starting capturing images.

2. The method of claim 1, wherein upon completion of lighting the first projection device, triggering the second projection device to initiate lighting comprises:
   upon completion of lighting, the first projection device transmitting a first projection trigger signal to the second projection device; and
   upon receiving the first projection trigger signal, the second projection device initiating lighting.

3. The method of claim 1, wherein:
   the first projection device takes a first duration from initiating lighting to completing lighting;
   the second projection device takes a second duration from initiating lighting to completing lighting; and
   the first delay circuit delays the first camera trigger signal for a time exceeding a sum of the first duration and the second duration.

4. The method of claim 1, wherein a first predetermined pattern projected by the first projection device and a third predetermined pattern projected by the third projection device are interleaved with each other, and a second predetermined pattern projected by the second projection device and a fourth predetermined pattern projected by the fourth projection device are interleaved with each other.

\* \* \* \* \*